United States Patent
Suthiwangcharoen et al.

(10) Patent No.: US 12,350,358 B2
(45) Date of Patent: *Jul. 8, 2025

(54) AQUEOUS CONDITIONER FORMULATION FOR THERMALLY STYLED HAIR

(71) Applicants: Dow Global Technologies LLC, Midland, MI (US); Rohm and Haas Company, Collegeville, PA (US); Dow Silicones Corporation, Midland, MI (US)

(72) Inventors: Nisaraporn Suthiwangcharoen, Midland, MI (US); Lyndsay M. Leal, Spring City, PA (US); Emmett M. Partain, III, Bound Brook, NJ (US); Nikhil J. Fernandes, Philadelphia, PA (US); Shannon Golden, Saginaw, MI (US); Bethany K Johnson, Midland, MI (US)

(73) Assignees: Dow Global Technologies LLC, Midland, MI (US); Rohm and Haas Company, Collegeville, PA (US); Dow Silicones Corporation, Midland, MI (US)

( * ) Notice: Subject to any disclaimer, the term of this patent is extended or adjusted under 35 U.S.C. 154(b) by 512 days.

This patent is subject to a terminal disclaimer.

(21) Appl. No.: 17/639,932

(22) PCT Filed: Oct. 26, 2020

(86) PCT No.: PCT/US2020/057295
§ 371 (c)(1),
(2) Date: Mar. 3, 2022

(87) PCT Pub. No.: WO2021/086773
PCT Pub. Date: May 6, 2021

(65) Prior Publication Data
US 2022/0331216 A1 Oct. 20, 2022

Related U.S. Application Data

(60) Provisional application No. 62/928,378, filed on Oct. 31, 2019.

(51) Int. Cl.
*A61K 8/41* (2006.01)
*A61Q 5/12* (2006.01)

(52) U.S. Cl.
CPC .............. *A61K 8/416* (2013.01); *A61Q 5/12* (2013.01)

(58) Field of Classification Search
CPC .................................. A61K 8/416; A61Q 5/12
See application file for complete search history.

(56) References Cited

U.S. PATENT DOCUMENTS

| | | | |
|---|---|---|---|
| 8,138,134 B2 | 3/2012 | Zhang et al. | |
| 8,790,627 B2 | 7/2014 | Erazo-Majewicz et al. | |
| 11,246,821 B2 | 2/2022 | Davis et al. | |
| 2004/0115155 A1 | 6/2004 | Salvador et al. | |
| 2004/0247550 A1* | 12/2004 | Asari | A61Q 19/00 424/70.12 |
| 2008/0003192 A1 | 1/2008 | Modi et al. | |
| 2008/0035167 A1* | 2/2008 | Chan | A45D 1/04 132/225 |

FOREIGN PATENT DOCUMENTS

| | | | |
|---|---|---|---|
| CN | 1259860 | 7/2000 | |
| CN | 1372455 | 10/2002 | |
| JP | 2000159642 A | 6/2000 | |
| WO | 2001034103 A1 | 5/2001 | |
| WO | 2002100360 A1 | 12/2002 | |
| WO | 2004108099 A2 | 12/2004 | |
| WO | WO-2008002666 A1 * | 1/2008 | ............ A61K 8/731 |
| WO | 2019025233 A1 | 2/2019 | |

OTHER PUBLICATIONS

Search Report from corresponding Chinese Application No. 202080072280.0 dated Jun. 8, 2023.

* cited by examiner

*Primary Examiner* — Blessing M Fubara
(74) *Attorney, Agent, or Firm* — Thomas S. Deibert

(57) ABSTRACT

An aqueous conditioner formulation for thermally styled hair is provided, including: an aqueous carrier; and a modified carbohydrate polymer, comprising a cellulose ether base material functionalized with (i) trialkyl ammonium moieties of formula (I)

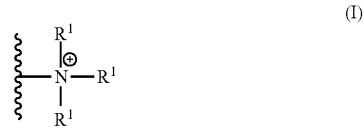

wherein $R^1$ is independently a $C_{1-7}$ alkyl group and wherein the modified carbohydrate polymer has a Kjeldahl nitrogen content, TKN, corrected for ash and volatiles, of 0.75 to 2.5 wt %; and (ii) hydrophobic substituents having 16 carbon atoms; wherein the modified carbohydrate polymer comprises 0.005 to 1.5 wt %, based on weight of the cellulose ether base material, of the hydrophobic substituents; wherein the hydrophobic substituents are randomly distributed across the backbone of the cellulose ether base material; wherein the cellulose ether base material has a weight average molecular weight, $M_w$, of >1,000,000 Daltons; and wherein the modified carbohydrate polymer has <0.001 wt %, based on weight of modified carbohydrate polymer, of crosslinking units.

14 Claims, No Drawings

AQUEOUS CONDITIONER FORMULATION FOR THERMALLY STYLED HAIR

The present invention relates to an aqueous conditioner formulation for thermally styled hair. In particular, the present invention relates to an aqueous conditioner formulation for thermally styled hair, comprising: a cosmetically acceptable aqueous carrier; and a modified carbohydrate polymer, comprising a cellulose ether base material functionalized with (i) trialkyl ammonium moieties of formula (I)

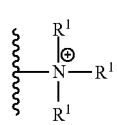

wherein each $R^1$ is independently a $C_{1-7}$ alkyl group and wherein the modified carbohydrate polymer has a Kjeldahl nitrogen content, TKN, corrected for ash and volatiles, of 0.75 to 2.5 wt %; and (ii) hydrophobic substituents having 16 carbon atoms; wherein the modified carbohydrate polymer comprises 0.005 to 1.5 wt %, based on weight of the cellulose ether base material, of the hydrophobic substituents; wherein the hydrophobic substituents are randomly distributed across the backbone of the cellulose ether base material; wherein the cellulose ether base material has a weight average molecular weight, $M_W$, of >1,000,000 Daltons; and wherein the modified carbohydrate polymer has <0.001 wt %, based on weight of modified carbohydrate polymer, of crosslinking units.

Conventional rinse off hair conditioners are popular with consumers for treating hair.

One hair conditioning composition is described by Salvador et al. in U.S. Patent Publication No. 20040115155. Salvador et al. disclose a hair conditioning composition comprising by weight (a) from about 0.001% to about 5% of a cellulose polymer having a molecular weight of about 10,000 to about 10,000,000; (b) from about 0.01% to about 10% of a cationic surfactant; (c) from about 0.01% to about 15% of a high melting point fatty compound having a melting point of 25° C. or higher; and (d) an aqueous carrier.

Notwithstanding, there remains a need for aqueous conditioner formulations for use on thermally styled hair that provide improved hair alignment.

The present invention provides an aqueous conditioner formulation for thermally styled hair, comprising: a cosmetically acceptable aqueous carrier; and a modified carbohydrate polymer, comprising a cellulose ether base material functionalized with (i) trialkyl ammonium moieties of formula (I)

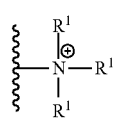

wherein each $R^1$ is independently selected from the group consisting of a $C_{1-7}$ alkyl group and wherein the modified carbohydrate polymer has a Kjeldahl nitrogen content, TKN, corrected for ash and volatiles, of 0.75 to 2.5 wt %; and (ii) hydrophobic substituents each having 16 carbon atoms; wherein the modified carbohydrate polymer comprises 0.005 to 1.5 wt %, based on weight of the cellulose ether base material, of the hydrophobic substituents; wherein the hydrophobic substituents are randomly distributed across the backbone of the cellulose ether base material; wherein the cellulose ether base material has a weight average molecular weight, $M_W$, of >1,000,000 Daltons; and wherein the modified carbohydrate polymer comprises <0.001 wt %, based on weight of modified carbohydrate polymer, of crosslinking units.

The present invention provides a method of making an aqueous conditioner formulation for thermally styled hair, comprising: (a) providing a cosmetically acceptable aqueous carrier; (b) selecting a hair alignment enhancer for improving hair alignment, wherein the hair alignment enhancer is selected to be a modified carbohydrate polymer; wherein the modified carbohydrate polymer comprises a cellulose ether base material functionalized with (i) trialkyl ammonium moieties of formula (I), wherein each $R^1$ is independently selected from the group consisting of a $C_{1-7}$ alkyl group and wherein the modified carbohydrate polymer has a Kjeldahl nitrogen content, TKN, corrected for ash and volatiles, of 0.75 to 2.5 wt %; and (ii) hydrophobic substituents each having 16 carbon atoms; wherein the modified carbohydrate polymer comprises 0.005 to 1.5 wt %, based on weight of the cellulose ether base material, of the hydrophobic substituents; wherein the hydrophobic substituents are randomly distributed across the backbone of the cellulose ether base material; wherein the cellulose ether base material has a weight average molecular weight, $M_W$, of >1,000,000 Daltons; and wherein the modified carbohydrate polymer comprises <0.001 wt %, based on weight of modified carbohydrate polymer, of crosslinking units; and (c) providing the selected hair alignment enhancer; and (d) combining the cosmetically acceptable aqueous carrier and the hair alignment enhancer; wherein the aqueous conditioner formulation contains 0.1 to 5 wt %, based on weight of the aqueous conditioner formulation, of the hair alignment enhancer.

The present invention provides a method of maintaining thermally styled hair, comprising: providing an aqueous conditioner formulation according to the present invention, applying the aqueous conditioner formulation to hair of a mammal and thermally styling the hair.

DETAILED DESCRIPTION

We have surprisingly found that hair alignment for thermally styled hair can be significantly improved following treatment with an aqueous conditioner formulation specifically selected to include a modified carbohydrate polymer, comprising a cellulose ether base material functionalized with (i) trialkyl ammonium moieties of formula (I)

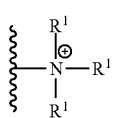

wherein each $R^1$ is independently selected from the group consisting of a $C_{1-7}$ alkyl group and wherein the modified carbohydrate polymer has a Kjeldahl nitrogen content, TKN, corrected for ash and volatiles, of 0.75 to 2.5 wt %; and (ii) hydrophobic substituents each having 16 carbon atoms; wherein the modified carbohydrate polymer comprises 0.005 to 1.5 wt %, based on weight of the cellulose ether base material, of the hydrophobic substituents; wherein the hydrophobic substituents are randomly distributed across the backbone of the cellulose ether base material; wherein the cellulose ether base material has a weight average molecular weight, $M_W$, of >1,000,000 Daltons; and wherein the modified carbohydrate polymer comprises <0.001 wt %, based on weight of modified carbohydrate polymer, of crosslinking units; such that the treated hair retains its shape even after incubating at 25° C. in a 50% humidity environment for a week.

Unless otherwise indicated, ratios, percentages, parts, and the like are by weight.

As used herein, unless otherwise indicated, the phrase "molecular weight" or $M_W$ refers to the weight average molecular weight as measured in a conventional manner with gel permeation chromatography (GPC) and conventional standards, such as polyethylene glycol standards. GPC techniques are discussed in detail in Modem Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Molecular weights are reported herein in units of Daltons, or equivalently, g/mol.

The term "cosmetically acceptable" as used herein and in the appended claims refers to ingredients typically used in personal care compositions, and is intended to underscore that materials that are toxic when present in the amounts typically found in personal care compositions are not contemplated as part of the present invention.

Preferably, the aqueous conditioner formulation for thermally styled hair of the present invention is selected from the group consisting of a shampoo, a conditioning shampoo, a leave on hair conditioner, a rinse off hair conditioner, a hair coloring agent, a hair styling gel and a hair straightener. More preferably, the aqueous conditioner formulation for thermally styled hair of the present invention is selected from the group consisting of a shampoo, a conditioning shampoo, a leave on hair conditioner and a rinse off hair conditioner. Most preferably, the aqueous conditioner formulation for thermally styled hair of the present invention is a rinse off conditioner.

Preferably, the aqueous conditioner formulation for thermally styled hair of the present invention, comprises: a cosmetically acceptable aqueous carrier (preferably, wherein the aqueous conditioner formulation comprises 25 to 99 wt % (preferably, 50 to 98.5 wt %; more preferably, 75 to 98 wt %; most preferably, 80 to 97 wt %), based on weight of the aqueous conditioner formulation, of the cosmetically acceptable aqueous carrier); a modified carbohydrate polymer (preferably, wherein the aqueous conditioner formulation comprises 0.1 to 5 wt % (preferably, 0.15 to 2 wt %; more preferably, 0.2 to 1 wt %; most preferably, 0.25 to 0.5 wt %), based on weight of the aqueous conditioner formulation, of the modified carbohydrate polymer), comprising a cellulose ether base material functionalized with (i) trialkyl ammonium moieties of formula (I)

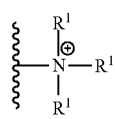

(I)

wherein each $R^1$ is independently selected from the group consisting of a $C_{1-7}$ alkyl group (preferably, a $C_{1-4}$ alkyl group; more preferably, a methyl group and an ethyl group; most preferably, a methyl group) and wherein the modified carbohydrate polymer has a Kjeldahl nitrogen content, TKN, corrected for ash and volatiles, of 0.75 to 2.5 wt % (preferably, 0.8 to 2.2 wt %; more preferably, 1.5 to 2.1 wt %; most preferably, 1.7 to 1.8 wt %); and (ii) hydrophobic substituents each having 16 carbon atoms; wherein the modified carbohydrate polymer comprises >0.005 to 1.5 wt % (preferably, 0.1 to 1.1 wt %; more preferably, 0.3 to <0.5 wt %; most preferably, 0.4 to 0.46 wt %), based on weight of the cellulose ether base material, of the hydrophobic substituents; wherein the hydrophobic substituents are randomly distributed across the backbone of the cellulose ether base material; wherein the cellulose ether base material has a weight average molecular weight, $M_W$, of >1,000,000 Daltons (preferably, 1,100,000 to 4,000,000 Daltons; more preferably, 1,200,000 to 2,000,000 Daltons; most preferably, 1,300,000 to 1,800,000 Daltons); and wherein the modified carbohydrate polymer comprises <0.001 wt % (preferably, <0.0001 wt %; more preferably, <0.00001 wt %; most preferably, less than the detectable limit), based on weight of modified carbohydrate polymer, of crosslinking units.

Preferably, the aqueous conditioner formulation for thermally styled hair of the present invention comprise, comprises a cosmetically acceptable aqueous carrier. More preferably, the aqueous conditioner formulation of the present invention, comprises: 25 to 99 wt % (preferably, 50 to 98.5 wt %; more preferably, 75 to 98 wt %; most preferably, 80 to 97 wt %), based on weight of the aqueous conditioner formulation, of the cosmetically acceptable aqueous carrier. Most preferably, the aqueous conditioner formulation of the present invention, comprises: 25 to 99 wt % (preferably, 50 to 98.5 wt %; more preferably, 75 to 98 wt %; most preferably, 80 to 97 wt %), based on weight of the aqueous conditioner formulation, of the cosmetically acceptable aqueous carrier; wherein the cosmetically acceptable carrier comprises water.

Preferably, the water used in the aqueous conditioner formulation of the present invention is at least one of distilled water and deionized water. More preferably, the water used in the aqueous conditioner formulation of the present invention is distilled and deionized.

Preferably, the aqueous conditioner formulation for thermally styled hair of the present invention comprises a modified carbohydrate polymer. More preferably, the aqueous conditioner formulation of the present invention comprises 0.1 to 5 wt % (preferably, 0.15 to 2 wt %; more preferably, 0.2 to 1 wt %; most preferably, 0.25 to 0.5 wt %), based on weight of the aqueous conditioner formulation, of a modified carbohydrate polymer. Most preferably, the aqueous conditioner formulation of the present invention comprises 0.1 to 5 wt % (preferably, 0.15 to 2 wt %; more preferably, 0.2 to 1 wt %; most preferably, 0.25 to 0.5 wt %), based on weight of the aqueous conditioner formulation, of a modified carbohydrate polymer; wherein the modified carbohydrate polymer comprises a cellulose ether base material functionalized with (i) trialkyl ammonium moieties of formula (I)

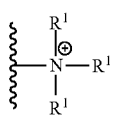

(I)

wherein each $R^1$ is independently selected from the group consisting of a $C_{1-7}$ alkyl group (preferably, a $C_{1-4}$ alkyl group; more preferably, a methyl group and an ethyl group; most preferably, a methyl group) and wherein the modified carbohydrate polymer has a Kjeldahl nitrogen content, TKN, corrected for ash and volatiles, of 0.75 to 2.5 wt % (preferably, 0.8 to 2.2 wt %; more preferably, 1.5 to 2.1 wt %; most preferably, 1.7 to 1.8 wt %); and (ii) hydrophobic substituents, wherein the hydrophobic substituents comprise an alkyl group having 16 carbon atoms; wherein the modified carbohydrate polymer comprises 0.005 to 1.5 wt % (preferably, 0.1 to 1.1 wt %; more preferably, 0.3 to <0.5 wt %; most preferably, 0.4 to 0.46 wt %), based on weight of the cellulose ether base material, of the hydrophobic substituents; wherein the hydrophobic substituents are randomly distributed across the backbone of the cellulose ether base material; wherein the cellulose ether base material has a weight average molecular weight, $M_W$, of >1,000,000 Daltons (preferably, 1,100,000 to 4,000,000 Daltons; more preferably, 1,200,000 to 2,000,000 Daltons; most preferably, 1,300,000 to 1,800,000 Daltons); and wherein the modified carbohydrate polymer comprises <0.001 wt % (preferably, <0.0001 wt %; more preferably, <0.00001 wt %; most preferably, less than the detectable limit), based on weight of modified carbohydrate polymer, of crosslinking units.

Preferably, the cellulose ether base material has a weight average molecular weight, $M_W$, of >1,000,000 Daltons (preferably, 1,100,000 to 4,000,000 Daltons; more preferably, 1,200,000 to 2,000,000 Daltons; most preferably, 1,300,000 to 1,800,000 Daltons). More preferably, the cellulose ether base material has a weight average molecular weight, $M_W$, of >1,000,000 Daltons (preferably, 1,100,000 to 4,000,000 Daltons; more preferably, 1,200,000 to 2,000,000 Daltons; most preferably, 1,300,000 to 1,800,000 Daltons); wherein the cellulose ether base material is selected from the group consisting of hydroxyethyl cellulose, hydroxypropyl cellulose, ethyl hydroxyethyl cellulose, methyl cellulose, hydroxypropyl methyl cellulose, hydroxyethyl methyl cellulose and mixtures thereof. Still more preferably, the cellulose ether base material has a weight average molecular weight, $M_W$, of >1,000,000 Daltons (preferably, 1,100,000 to 4,000,000 Daltons; more preferably, 1,200,000 to 2,000,000 Daltons; most preferably, 1,300,000 to 1,800,000 Daltons); wherein the cellulose ether base material is selected from the group consisting of hydroxyethyl cellulose, hydroxypropyl cellulose and mixtures thereof. Most preferably, the cellulose ether base material has a weight average molecular weight, $M_W$, of >1,000,000 Daltons (preferably, 1,100,000 to 4,000,000 Daltons; more preferably, 1,200,000 to 2,000,000 Daltons; most preferably, 1,300,000 to 1,800,000 Daltons); wherein the cellulose ether base material is hydroxyethyl cellulose.

Preferably, the aqueous conditioner formulation for thermally styled hair of the present invention comprises 0.1 to 5 wt % (preferably, 0.15 to 2 wt %; more preferably, 0.2 to 1 wt %; most preferably, 0.25 to 0.5 wt %), based on weight of the aqueous conditioner formulation, of a modified carbohydrate polymer; wherein the modified carbohydrate polymer comprises a cellulose ether base material functionalized with (i) trialkyl ammonium moieties of formula (I), wherein each $R^1$ is independently selected from the group consisting of a $C_{1-7}$ alkyl group (preferably, a $C_{1-4}$ alkyl group; more preferably, a methyl group and an ethyl group; most preferably, a methyl group) and wherein the modified carbohydrate polymer has a Kjeldahl nitrogen content corrected for ash and volatiles, TKN, of 0.75 to 2.5 wt % (preferably, 0.8 to 2.2 wt %; more preferably, 1.5 to 2.1 wt %; most preferably, 1.7 to 1.8 wt %). More preferably, the aqueous conditioner formulation for thermally styled hair of the present invention comprises 0.1 to 5 wt % (preferably, 0.15 to 2 wt %; more preferably, 0.2 to 1 wt %; most preferably, 0.25 to 0.5 wt %), based on weight of the aqueous conditioner formulation, of a modified carbohydrate polymer; wherein the modified carbohydrate polymer comprises a cellulose ether base material functionalized with (i) trialkyl ammonium moieties of formula (I), wherein each $R^1$ is independently selected from the group consisting of a $C_{1-7}$ alkyl group (preferably, a $C_{1-4}$ alkyl group; more preferably, a methyl group and an ethyl group; most preferably, a methyl group); wherein the modified carbohydrate polymer has a Kjeldahl nitrogen content corrected for ash and volatiles, TKN, of 0.75 to 2.5 wt % (preferably, 0.8 to 2.2 wt %; more preferably, 1.5 to 2.1 wt %; most preferably, 1.7 to 1.8 wt %); and wherein the modified carbohydrate polymer contains <0.1 moles (preferably, <0.01 moles; more preferably, <0.001 moles; most preferably, less than a detectable limit) of trialkyl ammonium moieties having formal (II) per mole of the cellulose ether base material

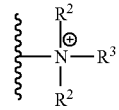

(II)

wherein each $R^2$ is independently selected from a methyl group and an ethyl group and wherein $R^3$ is selected from a $C_{8-30}$ alkyl group.

Preferably, the aqueous conditioner formulation for thermally styled hair of the present invention, comprises 0.1 to 5 wt % (preferably, 0.15 to 2 wt %; more preferably, 0.2 to 1 wt %; most preferably, 0.25 to 0.5 wt %), based on weight of the aqueous conditioner formulation, of a modified carbohydrate polymer; wherein the modified carbohydrate polymer comprises a cellulose ether base material functionalized with (ii) hydrophobic substituents, wherein the hydrophobic substituents comprise an alkyl group having 16 carbon atoms; wherein the modified carbohydrate polymer comprises 0.005 to 1.5 wt % (preferably, 0.1 to 1.1 wt %; more preferably, 0.3 to <0.5 wt %; most preferably, 0.4 to 0.46 wt %), based on weight of the cellulose ether base material, of the hydrophobic substituents. More preferably, the aqueous conditioner formulation of the present invention, comprises 0.1 to 5 wt % (preferably, 0.15 to 2 wt %; more preferably, 0.2 to 1 wt %; most preferably, 0.25 to 0.5 wt %), based on weight of the aqueous conditioner formulation, of a modified carbohydrate polymer; wherein the modified carbohydrate polymer comprises a cellulose ether base material functionalized with (ii) hydrophobic substituents, wherein the hydrophobic substituents comprise an alkyl group having 16 carbon atoms bonded to the cellulose ether base material through at least one of an ether linkage (e.g., an ether linkage alone or an ether linkage and a 2-hydroxypropyl group) and an ester linkage; wherein the modified carbohydrate polymer comprises 0.005 to 1.5 wt % (preferably, 0.1 to 1.1 wt %; more preferably, 0.3 to <0.5 wt %; most preferably, 0.4 to 0.46 wt %), based on weight of the cellulose ether base material, of the hydrophobic substituents. Still more preferably, the aqueous conditioner formulation of the present invention, comprises 0.1 to 5 wt % (preferably, 0.15 to 2 wt %; more preferably, 0.2 to 1 wt %; most preferably, 0.25 to 0.5 wt %), based on weight of the aqueous conditioner formulation, of a modified carbohydrate polymer; wherein the modified carbohydrate polymer comprises a cellulose ether base material functionalized with (ii) hydrophobic substituents, wherein the hydrophobic substituents comprise an alkyl group having 16 carbon atoms bonded to the water-soluble cellulose ether base material through at least one of an ether linkage (e.g., an ether linkage alone or an ether linkage and a 2-hydroxypropyl group) and an ester linkage; wherein the modified carbohydrate polymer comprises 0.005 to 1.5 wt % (preferably, 0.1 to 1.1 wt %; more preferably, 0.3 to <0.5 wt %; most preferably, 0.4 to 0.46 wt %), based on weight of the cellulose ether base material, of the hydrophobic substituents; and wherein the hydrophobic groups are randomly distributed across the backbone of the cellulose ether base material. Most preferably, the personal care composition of the present invention, comprises 0.1 to 5 wt % (preferably, 0.15 to 2 wt %; more preferably, 0.2 to 1 wt %; most preferably, 0.25 to 0.5 wt %), based on weight of the aqueous conditioner formulation, of a modified carbohydrate polymer; wherein the modified carbohydrate polymer comprises a cellulose ether base material functionalized with (ii) hydrophobic substituents, wherein the hydrophobic substituents comprise an alkyl group having 16 carbon atoms bonded to the water-soluble cellulose ether base material through at least one of an ether linkage or an ether linkage and a 2-hydroxypropyl group; wherein the modified carbohydrate polymer comprises comprises 0.005 to 1.5 wt % (preferably, 0.1 to 1.1 wt %; more preferably, 0.3 to <0.5 wt %; most preferably, 0.4 to 0.46 wt %), based on weight of the cellulose ether base material, of the hydrophobic substituents; and wherein the hydrophobic groups are randomly distributed across the backbone of the cellulose ether base material.

Preferably, the modified carbohydrate polymer is of formula (III)

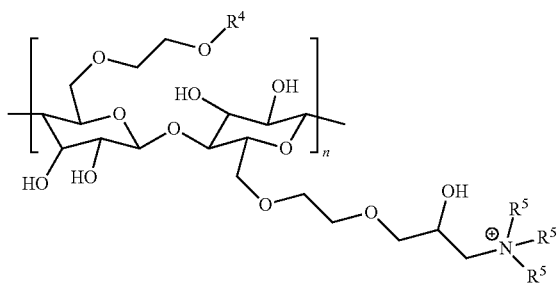

(III)

wherein n is determined based on the weight average molecular weight, $M_W$, of the cellulose ether base material; wherein $R^4$ is selected from the group consisting of an alkyl group having 16 carbon atoms and the residue of a $C_{16}$ alkyl glycidyl ether; and wherein each $R^5$ is independently selected from the group consisting of a $C_{1-7}$ alkyl group (preferably, a $C_{1-4}$ alkyl group; more preferably, a methyl group and an ethyl group; most preferably, a methyl group); and wherein the cellulose ether base material has a weight average molecular weight, $M_W$, of >1,000,000 Daltons (preferably, 1,100,000 to 4,000,000 Daltons; more preferably, 1,200,000 to 2,000,000 Daltons; most preferably, 1,300,000 to 1,800,000 Daltons); and wherein the modified carbohydrate polymer comprises <0.001 wt % (preferably, <0.0001 wt %; more preferably, <0.00001 wt %; most preferably, less than the detectable limit), based on weight of modified carbohydrate polymer, of crosslinking units.

Preferably, the aqueous conditioner for thermally styled hair of the present invention, optionally, further comprises at least one additional ingredient selected from the group consisting of a cosmetically acceptable cleansing surfactant; a thickener (e.g., polysaccharides, cellulosic polymers); a soap; a colorant; pH adjusting agent; an antioxidant (e.g., butylated hydroxytoluene); an emollient (polyoxyethylene glycol ($C_{7-20}$) fatty acid, esters of glycerol—e.g., PEG-7 glyceryl cocoate, PEG-30 glyceryl cocoate, PEG-12 glyceryl laureate, PEG-20 glyceryl oleate); a wax; a foaming agent; an emulsifying agent (e.g. PEG-100 stearate & glyceryl stearate mixture); a colorant; a fragrance; a chelating agent (e.g., disodium EDTA, tetrasodium EDTA, citric acid, lactic acid); an antimicrobial agent/preservative (e.g., methylchloroisothiazolinone, phenoxyethanol, methylisothiazolinone, esters of parabenzoic acid, diazolidinyl urea and imidazolidinyl urea, benzoic acid, sorbic acid); a bleaching agent; a lubricating agent; a sensory modifier; a sunscreen additive; a vitamin; a protein/amino acid; a plant extract; a natural ingredient; a bioactive agent; an anti-aging agent; a pigment; an acid; a penetrant; an anti-static agent; an anti-frizz agent; an antidandruff agent; a hair waving/straightening agent; a hair styling agent; a hair oil; an absorbent; a hard particle; a soft particle; a conditioning agent (e.g., guar hydroxypropyltrimonium chloride, PQ-10, PQ-7); a slip agent; an opacifier; a pearlizing agent and a salt. More preferably, the personal care composition of the present invention, optionally, further comprises at least one additional ingredient selected from the group consisting of an emulsifying agent (e.g. PEG-100 stearate & glyceryl stearate mixture); an antimicrobial agent/preservative (e.g., methylchloroisothiazolinone, phenoxyethanol, methylisothiazolinone, esters of parabenzoic acid, diazolidinyl urea and imidazolidinyl urea, benzoic acid, sorbic acid); a thickener (e.g., polysaccharides, cellulosic polymers); and a chelating agent (e.g., disodium EDTA, tetrasodium EDTA, citric acid, lactic acid). Most preferably, the personal care composition of the present invention, optionally, further comprises at least one additional ingredient selected from the group consisting of an emulsifying agent mixture of PEG-100 stearate & glyceryl stearate mixture; a hydroxyethyl cellulose polymer thickener; cetearyl alcohol emollient; tetrasodium ethylene diamine tetraacetic acid chelating agent and a mixture of phenoxyethanol and methylisothiazolinone preservative.

Preferably, the aqueous conditioner formulation for thermally styled hair of the present invention optionally further comprises an emulsifying agent. More preferably, the aqueous conditioner formulation for thermally styled hair of the present invention optionally further comprises 0.01 to 80 wt % (more preferably, 0.1 to 5 wt %; still more preferably, 0.5 to 2 wt %, most preferably, 0.75 to 1.25 wt %), based on weight of the aqueous conditioner formulation, of an emulsifying agent. Most preferably, the aqueous conditioner formulation of the present invention further comprises 0.01 to 80 wt % (more preferably, 0.1 to 5 wt %; still more preferably, 0.5 to 2 wt %, most preferably, 0.75 to 1.25 wt %), based on weight of the aqueous conditioner formulation, of an emulsifying agent; wherein the aqueous conditioner formulation is selected from the group consisting of a leave on hair conditioner and a rinse off hair conditioner; and wherein the emulsifying agent comprises a mixture of PET-100 stearate and glyceryl stearate.

Preferably, the aqueous conditioner formulation for thermally styled hair of the present invention optionally further comprises a thickener. More preferably, the aqueous conditioner formulation further comprises a thickener, wherein the thickener is selected to increase the viscosity of the aqueous conditioner formulation, preferably without substantially modifying the other properties of the personal care composition. Preferably, the aqueous conditioner formulation of the present invention further comprises a thickener, wherein the thickener is selected to increase the viscosity of the personal care composition, preferably without substantially modifying the other properties of the personal care composition and wherein the thickener accounts for 0 to 5.0 wt % (preferably, 0.1 to 5.0 wt %; more preferably, 0.2 to 2.5 wt %; most preferably, 0.5 to 2.0 wt %), based on weight of the aqueous conditioner formulation. Preferred thickeners include polysaccharides and cellulosic polymers. Preferably, the thickener is a hydroxyether cellulose polymer.

Preferably, the aqueous conditioner formulation for thermally styled hair of the present invention optionally further comprises a chelating agent. More preferably, the aqueous conditioner formulation further comprises 0.001 to 0.75 wt % (preferably, 0.03 to 0.25 wt %), based on weight of the aqueous conditioner formulation, of a chelating agent, wherein the chelating agent is selected from the group consisting of disodium ethylenediaminetetraacetic acid (EDTA), tetrasodium EDTA, citric acid, lactic acid and mixtures thereof. Most preferably, the aqueous conditioner formulation of the present invention further comprises 0.001 to 0.75 wt % (preferably, 0.03 to 0.25 wt %), based on weight of the aqueous conditioner formulation, of a chelating agent, wherein the chelating agent, wherein the chelating agent includes tetrasodium EDTA.

Preferably, the aqueous conditioner formulation for thermally styled hair of the present invention optionally further comprises an antimicrobial agent/preservative. More preferably, aqueous conditioner formulation for thermally styled hair of the present invention optionally further comprises 0.05 to 1.25 wt % (preferably, 0.1 to 1 wt %; more preferably, 0.25 to 0.75 wt %), based on weight of the aqueous conditioner formulation, of an antimicrobial agent/preservative; wherein the antimicrobial/preservative is selected from the group consisting of phenoxyethanol, benzoic acid, benzyl alcohol, sodium benzoate, DMDM hydantoin, 2-ethylhexyl glyceryl ether, isothiazolinone (e.g., methylchloroisothiazolinone, methylisothiazolinone) and mixtures thereof. Most preferably, the aqueous conditioner formulation for thermally styled hair of the present invention optionally further comprises 0.05 to 1.25 wt % (preferably, 0.1 to 1 wt %; more preferably, 0.25 to 0.75 wt %), based on weight of the aqueous conditioner formulation, of an antimicrobial agent/preservative; wherein the antimicrobial/preservative is a mixture of phenoxyethanol and an isothiazolinone (more preferably, wherein the antimicrobial/preservative is a mixture of phenoxyethanol and methylisothiazolinone).

Preferably, the method of making an aqueous conditioner formulation for thermally styled hair, comprises: (a) providing a cosmetically acceptable aqueous carrier (preferably, water); (b) selecting a hair alignment enhancer for improving hair alignment, wherein the hair alignment enhancer is selected to be a modified carbohydrate polymer; wherein the modified carbohydrate polymer comprises a cellulose ether base material functionalized with (i) trialkyl ammonium moieties of formula (I), wherein each $R^1$ is independently selected from the group consisting of a $C_{1-7}$ alkyl group (preferably, a $C_{1-4}$ alkyl group; more preferably, a methyl group and an ethyl group; most preferably, a methyl group) and wherein the modified carbohydrate polymer has a Kjeldahl nitrogen content, TKN, corrected for ash and volatiles, of 0.75 to 2.5 wt % (preferably, 0.8 to 2.2 wt %; more preferably, 1.5 to 2.1 wt %; most preferably, 1.7 to 1.8 wt %); and (ii) hydrophobic substituents each having 16 carbon atoms; wherein the modified carbohydrate polymer comprises 0.005 to <0.5 wt % (preferably, 0.1 to 0.49 wt %; more preferably, 0.3 to 0.48 wt %; most preferably, 0.4 to 0.46 wt %), based on weight of the cellulose ether base material, of the hydrophobic substituents; wherein the hydrophobic substituents are randomly distributed across the backbone of the cellulose ether base material; wherein the cellulose ether base material has a weight average molecular weight, $M_w$, of >1,000,000 Daltons (preferably, 1,100,000 to 4,000,000 Daltons; more preferably, 1,200,000 to 2,000,000 Daltons; most preferably, 1,300,000 to 1,800,000 Daltons); and wherein the modified carbohydrate polymer comprises <0.001 wt % (preferably, <0.0001 wt %; more preferably, <0.00001 wt %; most preferably, less than the detectable limit), based on weight of modified carbohydrate polymer, of crosslinking units; and (c) providing the selected hair alignment enhancer; and (d) combining the cosmetically acceptable aqueous carrier and the hair alignment enhancer; wherein the aqueous conditioner formulation contains 0.1 to 5 wt % (preferably, 0.15 to 3 wt %; more preferably, 0.2 to 1 wt %; most preferably, 0.25 to 0.5 wt %), based on weight of the aqueous conditioner formulation, of the hair alignment enhancer.

Preferably, the method of thermally styling hair of the present invention, comprises: providing an aqueous conditioner formulation of the present invention; applying the aqueous conditioner formulation to hair of a mammal; optionally, rinsing the aqueous conditioner formulation from the hair; and thermally styling the hair (preferably, thermally styling the hair with at least one of a hot iron and a thermally heated comb).

Some embodiments of the present invention will now be described in detail in the following Examples.

Comparative Example C1: Hydrophobically Modified Cellulose Ether Base Material

A 1,000 mL, four necked, round bottomed flask was charged with cellulose ether base material (69.83 g, CELLOSIZE™ QP-100MH hydroxyethyl cellulose available from The Dow Chemical Company), isopropyl alcohol (358.34 g) and deionized water (55.6 g). The flask was fitted with a nitrogen inlet connected to a 60 mL pressure equalizing addition funnel, rubber septum cap, a stirring paddle connected to an electric motor and a Claisen adaptor connected to a Friedrich condenser with a mineral oil bubbler outlet. The addition funnel was then charged with 1-bromododecane (8.01 g) in isopropyl alcohol (20 g). The stirring paddle was engaged and the head space in the flask was purged with a slow, steady flow of nitrogen (one bubble per second) for one hour to remove any entrained oxygen. Then a 50% aqueous sodium hydroxide solution (8.08 g) was added dropwise to the flask contents over two (2) minutes. The flask contents were left to stir for an hour following addition of the 50% sodium hydroxide solution. The 1-bromododecane in isopropyl alcohol solution in the addition funnel was then charged dropwise to the flask contents over three (3) minutes. The flask contents were left to stir for twenty (20) minutes following the addition of the 1-bromododecane in isopropyl alcohol. Then heat was applied to the contents of the flask using a heating mantle. The flask contents were allowed to reflux with continued stirring under nitrogen for four and a half (4.5) hours. The flask was then placed in an ice water bath while maintaining a positive nitrogen pressure in the flask to cool the flask contents. The flask contents were then neutralized via the addition thereto of glacial acetic acid (6.0 g) using a syringe. The flask contents were left to stir for ten (10) minutes under nitrogen. The flask contents were then vacuum filtered through a large fritted metal Buchner funnel to recover the hydrophobically modified cellulose ether base material. The recovered hydrophobically modified cellulose ether base material was then washed in the Buchner funnel by stirring in the funnel for five (5) minutes with the specified wash solvents followed by vacuum removal of the wash liquor: deionized water (108 g) in isopropyl alcohol (492 g); deionized water (60 g) in isopropyl alcohol (540 g); and then isopropyl alcohol (600 g) for desiccation. To confer cold-water dispersibility on the final polymer, a 40% aqueous glyoxal (1.44 g) and acetic acid (0.44 g) were added to the final desiccation wash. The washed product hydrophobically modified cellulose ether base material was then briefly air dried and then dried overnight in vacuo at 50° C. The dried product hydrophobically modified cellulose ether base material was then sieved through a #30 mesh US standard sieve and obtained as an off-white solid with a volatiles content of 3.11%, an ash content (as sodium acetate) of 5.43%. The 1% solution viscosity (corrected for ash and volatiles) was measured at 6.31 sec$^{-1}$ using a TA Instruments DHR-3 rheometer equipped with a 40 mm, 2.0° stainless steel cone & plate sensor at 25.0° C. and was found to be 11,095 mPa·s.

Comparative Example C2: Modified Carbohydrate Polymer

A 1,000 mL, four necked, round bottomed flask was charged with hydrophobically modified cellulose ether base material prepared according to Comparative Example C1 (68.76), isopropyl alcohol (505.44 g) and deionized water (90.39 g). The flask was fitted with a nitrogen inlet connected to a 60 mL pressure equalizing addition funnel, rubber septum cap, a stirring paddle connected to an electric motor and a Claisen adaptor connected to a Friedrich condenser with a mineral oil bubbler outlet. The addition funnel was then charged with 70% aqueous glycidyl trimethylammonium chloride (48.6 g, available from QUAB Chemicals under the trade name QUAB® 151). While stirring the flask contents, the apparatus was slowly purged with nitrogen for one hour to remove any entrained oxygen. After the nitrogen purge was completed, a 25% aqueous sodium hydroxide solution (7.72 g) was added to the flask contents with stirring under nitrogen through the serum cap using a plastic syringe over two minutes. After stirring for one hour, the contents of the addition funnel were added dropwise into the flask contents over three minutes. The flask contents were stirred under nitrogen for 20 minutes. Then heat was applied to the flask contents using the J-KEM controller with a set point temperature of 55° C. The flask contents were left to reflux for 1.5 hours with stirring under nitrogen. The flask contents were then cooled to room temperature while maintaining a positive nitrogen pressure in the flask. The flask contents were then neutralized by adding glacial acetic acid (7.5 g) by syringe. After stirring for 10 minutes, cationic hydrophobically modified hydroxyethyl cellulose polymer (cationic hmHEC polymer) was recovered from the flask contents by vacuum filtration through a metal fritted Buchner funnel. The recovered cationic hmHEC polymer was then washed in the Buchner funnel once each with the following: a mixture of isopropyl alcohol (492 g) and deionized water (108 g), a mixture of isopropyl alcohol (540 g) and deionized water (60 g) and a mixture of isopropyl alcohol (600 g), 40% glyoxal (1.32 g) and glacial acetic acid (0.46 g). The cationic hmHEC polymer was then briefly air dried and dried overnight in vacuo at 50° C. The dried cationic hmHEC polymer was then manually group using a mortar & pestle and screened through a #30 mesh US standard sieve to give 89.67 g of product cationic hmHEC polymer. The product cationic hmHEC polymer had a volatiles content of 8.89%, an ash content of 2.62% (as sodium chloride) and a Kjeldahl nitrogen content of 1.92%. The 1% solution viscosity (corrected for ash and volatiles) was measured at 6.31 sec$^{-1}$ using a TA Instruments DHR-3 rheometer equipped with a 40 mm, 2.0° stainless steel cone & plate sensor at 25.0° C. and was found to be 3,150 mPa·s.

Comparative Examples C3-C6 and Examples 1-6: Cationic hmHEC

The product cationic hydrophobically modified cellulose ether base material in each of Comparative Examples C3-C6 and Examples 1-6 was prepared using the same process as described above for Comparative Examples C1-C2, with appropriate changes in raw material charges to provide the product cationic hydrophobically modified cellulose ether base material with the (i) trimethyl ammonium moieties with Kjeldahl nitrogen, TKN; and (ii) the hydrophobic substituent with degree of substitution noted in TABLE 1.

TABLE 1

| | | | | Modified Carbohydrate Polymer | | | | | | |
|---|---|---|---|---|---|---|---|---|---|---|
| | | | | Hydrophobic Substituents | | cationic substituents* | | Properties | | |
| | Base material | | | | DS | | DS | | | Viscosity |
| Ex. | Type | Mw (Daltons) | Type | Alkyl | (wt %) | (molar ratio) | TKN (wt %) | (molar ratio) | Volatiles (wt %) | Ash (wt %) | 6.31 sec$^{-1}$ (mPa·s) |
| C1 | A | $1.6 \times 10^6$ | X | $C_{12}$ | 0.94 | 0.014 | 0 | 0 | 3.11 | 5.43 | 11,095 |
| C2 | A | $1.6 \times 10^6$ | X | $C_{12}$ | 0.75 | 0.014 | 1.928 | 0.435 | 8.89 | 2.62 | 3,150 |
| C3 | A | $1.6 \times 10^6$ | Y | $C_8$ | 0.84 | 0.024 | 2.061 | 0.474 | 5.67 | 3.81 | 1,559 |
| C4 | B | $9 \times 10^4$ | Z | $C_{16}$ | 0.47 | 0.0074 | 2.67 | 0.671 | 1.11 | 5.15 | — |
| C5 | C | $3.7 \times 10^5$ | Z | $C_{16}$ | 0.49 | 0.0062 | 1.13 | 0.23 | 1.03 | 3.24 | — |
| C6 | D | $9 \times 10^5$ | Z | $C_{16}$ | 1.91 | 0.028 | 2.14 | 0.496 | 1.39 | 2.52 | — |
| 1 | E | $1.4 \times 10^6$ | Z | $C_{16}$ | 0.44 | 0.006 | 1.764 | 0.392 | 3.77 | 2.41 | 6,268 |
| 2 | E | $1.4 \times 10^6$ | Z | $C_{16}$ | 1.04 | 0.014 | 1.564 | 0.341 | 2.91 | 5.50 | 17,336 |
| 3 | E | $1.4 \times 10^6$ | Z | $C_{16}$ | 0.4 | 0.006 | 2.319 | 0.556 | 3.84 | 3.48 | 3,324 |
| 4 | E | $1.4 \times 10^6$ | Z | $C_{16}$ | 0.49 | 0.006 | 0.856 | 0.169 | 3.08 | 3.41 | 10,671 |

TABLE 1-continued

| | | | Modified Carbohydrate Polymer | | | | | | |
|---|---|---|---|---|---|---|---|---|---|
| | Base material | | Hydrophobic Substituents | | cationic substituents* | | Properties | | |
| Ex. | Type | Mw (Daltons) | Type | Alkyl (wt %) | DS (molar ratio) | TKN (wt %) | DS (molar ratio) | Volatiles (wt %) | Ash (wt %) | Viscosity 6.31 sec$^{-1}$ (mPa · s) |
| 5 | E | $1.4 \times 10^6$ | Z | $C_{16}$ 0.73 | 0.01 | 1.743 | 0.387 | 3.60 | 2.74 | 12,407 |
| 6 | A | $1.6 \times 10^6$ | Z | $C_{16}$ 0.97 | 0.014 | 2.056 | 0.4782 | 3.17 | 6.89 | 17,331 |

*trimethyl ammonium residues from glycidyl trimethylammonium chloride (QUAB® 151 from QUAB Chemicals)
A CELLOSIZE™ QP-100MH hydroxyethyl cellulose with a weight average molecular weight, Mw, of 1,6000,000 from The Dow Chemical Company
B CELLOSIZE™ EP-09 hydroxyethyl cellulose with a weight average molecular weight, Mw, of 90,000 from The Dow Chemical Company
C CELLOSIZE™ AM-103 hydroxyethyl cellulose with a weight average molecular weight, Mw, of 370,000 from The Dow Chemical Company
D CELLOSIZE™ QP-4400H hydroxyethyl cellulose with a weight average molecular weight, Mw, of 900,000 from The Dow Chemical Company
E CELLOSIZE™ QP-52,000H hydroxyethyl cellulose with a weight average molecular weight, Mw, of 1,400,000 from The Dow Chemical Company
X 1-bromododecane
Y 1-bromooctane
Z 1-bromohexadecane Comparative Examples CF1-CF9 and Examples F1-F6: Rinse Off Conditioner A rinse off conditioner formulation was prepared in each of Comparative Examples CF1-CF9 and Examples F1-F6 using the rinse off conditioner formulation noted in TABLE 2.

TABLE 2

| Ingredient INCI name | wt % |
|---|---|
| Deionized water | q.s. 100 |
| Hydroxyethyl Cellulose[1] | 0.2 |
| Polymer | 0.3 |
| Tetrasodium EDTA[2] | 0.2 |
| Cetearyl Alcohol[3] | 1.0 |
| PEG-100 Stearate & Glyceryl Stearate[4] | 1.0 |
| Phenoxyethanol and Methylisothiazolinone[5] | 0.5 |

[1]available from The Dow Chemical Company under the tradename CELLOSIZE™ PCG-10 Europe
[2]available from The Dow Chemical Company under tradename Versene™ 220
[3]available from Croda Inc. under tradename Crodacol CS-50
[4]available from Croda Inc. under tradename Arlacel 165
[5]preservative available from The Dow Chemical Company under tradename Neolone™ PE The shampoo formulation was prepared in each of Comparative Examples CF1-CF9 and Examples F1-F6 using the following process: Deionized water was added to a 250 mL beaker and heated to 70° C. with constant stirring. The hydroxyethyl cellulose thickener was then added to the beaker with continued stirring and heating until homogeneously thickened. Then the cetearyl alcohol and the PEG-stearate & glyceryl stearate and the Polymer noted in TABLE 3 were added to the beaker over three minutes. Then the tetrasodium ethylenediamine tetra acetic acid was added to the beaker over three minutes after which the heat source was removed and mixing continued until the temperature of the beaker contents was below 40° C. Then the PEG-100 stearate & glyceryl stearate and phenoxyethanol and methylisothiazolinone were added to the beaker. The final pH of the product shampoo formulation was then adjusted to a pH of 5.5 using sodium hydroxide or citric acid as necessary and sufficient water was added to adjust the total formulation weight to 100 g.

TABLE 3

| Rinse Off Conditioner Formulation | Polymer |
|---|---|
| Comparative Example CF1 | Comp. Example C2 |
| Comparative Example CF2 | Comp. Example C3 |
| Comparative Example CF3 | Polyquaternium-10[1] |
| Comparative Example CF4 | Polyquaternium-67[2] |
| Comparative Example CF5 | — |
| Comparative Example CF6 | Polyquaternium-67[3] |
| Comparative Example CF7 | Comp. Example C4 |
| Comparative Example CF8 | Comp. Example C5 |
| Comparative Example CF9 | Comp. Example C6 |
| Example F1 | Example 1 |
| Example F2 | Example 2 |
| Example F3 | Example 3 |
| Example F4 | Example 4 |
| Example F5 | Example 5 |
| Example F6 | Example 6 |

[1]commercially available from The Dow Chemical Company under tradename UCARE™ Polymer JR-30M
[2]commercially available from The Dow Chemical Company under tradename SoftCat™ SX1300X
[3]commercially available from The Dow Chemical Company under tradename SoftCat™ SL5

Hair Treatment Tests

Unless otherwise specified, the following hair treatment experiments were performed using darkly bleached tresses (2 g) purchased from International Hair Importers & Products, Inc. Each experiment was done in triplicate with the average result provided. Each tress was first rinsed with tap water for 30 seconds, washed with a 9% sodium lauryl sulfate (SLS; 0.2 g/g of hair) for 30 seconds, rinsed with tap water for 1 minute, treated with a rinse off conditioner noted in TABLES 4-7 (0.4 g/g of hair) for 1 min, and rinsed with tap water for 30 seconds. The treated tresses were then air dried at room temperature overnight prior to analyses.

Dry/Wet Combing

Dry/Wet combing was performance was measured using an Instron Model 4464 and BlueHill 2 software. Reference STP PC 045. The Dry/Wet combing performance was done using two different lots of hair with results for the different lots provided in a separate table. The results are provided in TABLES 4-5.

TABLE 4

| Rinse Off Conditioner | Combing Load (kgf) | |
|---|---|---|
|  | Dry | Wet |
| Comp. Example CF1 | 0.138 | 0.111 |
| Comp. Example CF2 | 0.124 | 0.114 |
| Comp. Example CF3 | 0.152 | 0.102 |
| Comp. Example CF4 | 0.129 | 0.086 |
| Comp. Example CF5 | 0.904 | 2.257 |
| Comp. Example CF7 | 0.0616 | 0.1206 |
| Comp. Example CF8 | 0.0478 | 0.0549 |
| Comp. Example CF9 | 0.0528 | 0.0408 |
| Example F1 | 0.0550 | 0.0400 |
| Example F2 | 0.0480 | 0.0390 |

TABLE 5

| Rinse Off Conditioner | Combing Load (kgf) | |
|---|---|---|
|  | Dry | Wet |
| Example F1 | 0.0290 | 0.0317 |
| Example F3 | 0.0245 | 0.0393 |
| Example F4 | 0.0256 | 0.0367 |
| Example F5 | 0.0307 | 0.0454 |
| Example F6 | 0.0338 | 0.0357 |
| Comp. Example CF5 | 0.0470 | 0.9320 |

Reduced Breakage

Reduced breakage performance was measured using repeated combing instrument. 10,000 comb strokes; speed: 20 cycles/min (80 comb strokes/tress/min). Percent reduction was calculated from the weight difference of the treated hair tresses before and after combing. The results are provided in TABLE 6.

TABLE 6

| Rinse Off Conditioner | % Breakage Reduction |
|---|---|
| Comp. Example CF1 | 98.02 |
| Example F1 | 90.98 |
| Comp. Example CF3 | 61.32 |
| Comp. Example CF4 | 97.38 |
| Comp. Example CF6 | 66.73 |

Hair Alignment

Hair alignment performance was measured using Frizzy Type A hair. The treated hair tresses were thermally straightened using a hair straightener applied on each tress at 200° C. for a total of 10 passes with 10 seconds each pass. Hair alignment and orientation styling was measured using RUMBA-Bossa Nova with the alignment coefficient reported for after 0, 3, 6 and 10 passes. The results are provided in TABLE 7.

TABLE 7

| Rinse Off Conditioner | Alignment Coefficient | | | |
|---|---|---|---|---|
|  | 0 Passes | 3 Passes | 6 Passes | 10 Passes |
| Example F1 | 33.22 | 50.97 | 58.43 | 60.42 |
| Comp. Example CF3 | 9.49 | 20.79 | 25.78 | 41.38 |
| Comp. Example CF4 | 17.65 | 42.66 | 46.29 | 43.12 |
| Comp. Example CF5 | 19.55 | 33.08 | 37.06 | 41.14 |

We claim:

1. An aqueous conditioner formulation for thermally styled hair, comprising:
a cosmetically acceptable aqueous carrier; and
a modified carbohydrate polymer, comprising a cellulose ether base material functionalized with (i) trialkyl ammonium moieties of formula (I)

wherein each $R^1$ is independently selected from the group consisting of a $C_{1-7}$ alkyl group and wherein the modified carbohydrate polymer has a Kjeldahl nitrogen content, TKN, corrected for ash and volatiles, of 1.5 to 2.2 wt %; and (ii) hydrophobic substituents each having 16 carbon atoms; wherein the modified carbohydrate polymer comprises 0.1 to 1.1 wt %, based on weight of the cellulose ether base material, of the hydrophobic substituents; wherein the hydrophobic substituents are randomly distributed across the backbone of the cellulose ether base material; wherein the cellulose ether base material has a weight average molecular weight, $M_w$, of 1,100,000 to 4,000,000 Daltons; and wherein the modified carbohydrate polymer comprises <0.001 wt %, based on weight of modified carbohydrate polymer, of crosslinking units.

2. The aqueous conditioner formulation of claim 1, further comprising a thickener.

3. The aqueous conditioner formulation of claim 2, wherein the thickener is a polysaccharide.

4. The aqueous conditioner formulation of claim 1, wherein the hydrophobic substituent is bonded to the cellulose ether base material through an ether linkage or an ether linkage and a 2-hydroxypropyl group.

5. The aqueous conditioner formulation of claim 1, further comprising a chelating agent.

6. The aqueous conditioner formulation of claim 1, further comprising a preservative.

7. The aqueous conditioner formulation of claim 1, further comprising an emollient.

8. The aqueous conditioner formulation of claim 1, further comprising a cosmetically acceptable cleansing surfactant.

9. A method of thermally styling hair, comprising:
providing an aqueous conditioner formulation according to claim 1,
applying the aqueous conditioner formulation to hair of a mammal, and
thermally styling the hair.

10. The method of claim 9, wherein the hair is Frizzy Type A hair and wherein thermally styling the hair is thermally straightening the hair.

11. An aqueous conditioner formulation for thermally straightened frizzy hair, comprising:
a cosmetically acceptable aqueous carrier; and
a modified carbohydrate polymer, comprising a cellulose ether base material functionalized with (i) trialkyl ammonium moieties of formula (I)

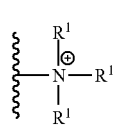

(I)

wherein each $R^1$ is independently selected from the group consisting of a $C_{1-7}$ alkyl group and wherein the modified carbohydrate polymer has a Kjeldahl nitrogen content, TKN, corrected for ash and volatiles, of 1.5 to 2.2 wt %; and (ii) hydrophobic substituents each having 16 carbon atoms; wherein the modified carbohydrate polymer comprises 0.1 to 1.1 wt %, based on weight of the cellulose ether base material, of the hydrophobic substituents; wherein the hydrophobic substituents are randomly distributed across the backbone of the cellulose ether base material; wherein the cellulose ether base material has a weight average molecular weight, $M_W$, of 1,100,000 to 4,000,000 Daltons; and wherein the modified carbohydrate polymer comprises <0.001 wt %, based on weight of modified carbohydrate polymer, of crosslinking units.

12. The aqueous conditioner formulation of claim 11, wherein the modified carbohydrate polymer has a Kjeldahl nitrogen content, TKN, corrected for ash and volatiles, of 1.7 to 1.8 wt %; wherein the modified carbohydrate polymer comprises 0.3 to <0.5 wt %, based on weight of the cellulose ether base material, of hydrophobic substituents; and wherein the cellulose ether base material has a weight average molecular weight, $M_W$, of 1,200,000 to 2,000,000 Daltons.

13. The aqueous conditioner formulation of claim 11, wherein the modified carbohydrate polymer comprises 0.4 to 0.46 wt %, based on weight of the cellulose ether base material, of the hydrophobic substituents; and wherein the cellulose ether base material has a weight average molecular weight, $M_W$, of 1,300,000 to 1,800,000 Daltons.

14. A method of making an aqueous conditioner formulation for thermally styled hair, comprising:
(a) providing a cosmetically acceptable aqueous carrier;
(b) selecting a hair alignment enhancer for improving hair alignment, wherein the hair alignment enhancer is selected to be a modified carbohydrate polymer; wherein the modified carbohydrate polymer comprises a cellulose ether base material functionalized with
(i) trialkyl ammonium moieties of formula (I)

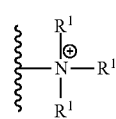

(I)

wherein each $R^1$ is independently selected from the group consisting of a $C_{1-7}$ alkyl group and wherein the modified carbohydrate polymer has a Kjeldahl nitrogen content, TKN, corrected for ash and volatiles, of 1.5 to 2.2 wt %; and
(ii) hydrophobic substituents each having 16 carbon atoms; wherein the modified carbohydrate polymer comprises 0.1 to 1.1 wt %, based on weight of the cellulose ether base material, of the hydrophobic substituents; wherein the hydrophobic substituents are randomly distributed across the backbone of the cellulose ether base material; wherein the cellulose ether base material has a weight average molecular weight, $M_W$, of 1,100,000 to 4,000,000 Daltons; and wherein the modified carbohydrate polymer comprises <0.001 wt %, based on weight of modified carbohydrate polymer, of crosslinking units; and
(c) providing the selected hair alignment enhancer; and
(d) combining the cosmetically acceptable aqueous carrier and the hair alignment enhancer;
wherein the aqueous conditioner formulation contains 0.1 to 5 wt %, based on weight of the aqueous conditioner formulation, of the hair alignment enhancer.

* * * * *